(12) United States Patent
Hjelle et al.

(10) Patent No.: US 9,763,602 B2
(45) Date of Patent: Sep. 19, 2017

(54) INTRA-OPERATIVE HEART SIZE MEASURING TOOL

(71) Applicant: Mardil, Inc., Plymouth, MN (US)

(72) Inventors: Aaron J. Hjelle, Andover, MN (US);
Robert G. Walsh, Lakeville, MN (US);
William E. Cohn, Bellaire, TX (US);
Louis Labrousse, Bordeaux (FR)

(73) Assignee: Mardil, Inc., Plymouth, MN (US)

( * ) Notice: Subject to any disclaimer, the term of this patent is extended or adjusted under 35 U.S.C. 154(b) by 0 days.

(21) Appl. No.: 15/223,973

(22) Filed: Jul. 29, 2016

(65) Prior Publication Data
US 2016/0345866 A1    Dec. 1, 2016

Related U.S. Application Data

(63) Continuation of application No. 14/698,689, filed on Apr. 28, 2015, now Pat. No. 9,427,318, which is a
(Continued)

(51) Int. Cl.
*A61B 5/107*      (2006.01)
*A61B 5/00*       (2006.01)
(Continued)

(52) U.S. Cl.
CPC .......... *A61B 5/1076* (2013.01); *A61B 5/0044* (2013.01); *A61B 5/107* (2013.01);
(Continued)

(58) Field of Classification Search
CPC ...... A61F 2/2481; A61F 2/2496; A61B 5/107; A61B 5/1076; A61B 19/46; A61B 2019/461
(Continued)

(56) References Cited

U.S. PATENT DOCUMENTS 5,613,302 A * 3/1997 Berman ................ G01B 5/025
                                              33/514.2
5,860,923 A * 1/1999 Lenker ............... A61B 5/02014
                                                600/433
(Continued)

FOREIGN PATENT DOCUMENTS

WO    WO 2008/003034    1/2008
WO    WO 2008/011411    1/2008

OTHER PUBLICATIONS

U.S. Appl. No. 14/698,689, filed Apr. 28, 2015, Hjelle et al.
(Continued)

*Primary Examiner* — Michael C Stout
(74) *Attorney, Agent, or Firm* — Fish & Richardson P.C.

(57) ABSTRACT

A heart size measuring tool includes a tubular body, a flexible measuring cord having length indicia, a measuring cord support mechanism movable between retracted and extended states with respect to the body, and an actuating mechanism to move the measuring cord support mechanism. When in the retracted state the measuring cord support mechanism is positioned within the tubular body with the measuring cord in a collapsed position. When the measuring cord support mechanism is in the extended state the measuring cord extends around a portion of a heart to be measured. A scale on the body can be used in connection with the indicia on the measurement cord to provide a reading of the heart size.

12 Claims, 10 Drawing Sheets

Related U.S. Application Data continuation of application No. 13/261,173, filed as application No. PCT/US2010/028830 on Mar. 26, 2010, now Pat. No. 9,044,169.

(60) Provisional application No. 61/164,183, filed on Mar. 27, 2009.

(51) Int. Cl.
*A61F 2/24* (2006.01)
*A61B 17/00* (2006.01)
*A61B 90/00* (2016.01)

(52) U.S. Cl.
CPC .......... *A61B 5/6846* (2013.01); *A61B 5/6869* (2013.01); *A61B 17/00234* (2013.01); *A61F 2/2481* (2013.01); *A61F 2/2496* (2013.01); *A61B 90/06* (2016.02); *A61B 2017/00238* (2013.01); *A61B 2017/00243* (2013.01); *A61B 2090/061* (2016.02)

(58) Field of Classification Search
USPC ................................................ 600/587–595
See application file for complete search history.

(56) References Cited

U.S. PATENT DOCUMENTS

| | | | |
|---|---|---|---|
| 6,110,200 A | | 8/2000 | Hinnenkamp |
| 6,179,791 B1* | | 1/2001 | Krueger ................. A61B 5/107 33/512 |
| 6,427,351 B1* | | 8/2002 | Matthews ............ A61B 5/1076 33/512 |
| 6,575,921 B2 | | 6/2003 | Vanden Hoek et al. |
| 6,613,002 B1* | | 9/2003 | Clark ................... A61B 5/1076 600/104 |
| 7,213,601 B2 | | 5/2007 | Stevens et al. |
| 7,651,462 B2 | | 1/2010 | Hjelle et al. |
| 2002/0111567 A1* | | 8/2002 | Vanden Hoek ........ A61B 5/107 600/587 |
| 2003/0074011 A1 | | 4/2003 | Gilboa et al. |
| 2004/0002626 A1* | | 1/2004 | Feld ................. A61B 17/00234 600/37 |
| 2004/0055608 A1* | | 3/2004 | Stevens ............ A61B 17/00234 128/898 |
| 2006/0021244 A1 | | 2/2006 | Oura |
| 2006/0064038 A1* | | 3/2006 | Omata ................... A61B 5/103 600/587 |
| 2007/0106181 A1* | | 5/2007 | Mangiardi ........... A61B 5/1076 600/587 |
| 2007/0197859 A1 | | 8/2007 | Schaer et al. |
| 2007/0255185 A1* | | 11/2007 | Dubey ................... A61B 5/036 600/591 |
| 2008/0033234 A1 | | 2/2008 | Hjelle et al. |
| 2008/0147076 A1 | | 6/2008 | Geisert et al. |
| 2009/0171358 A1* | | 7/2009 | Chang .................... A61B 5/417 606/63 |
| 2009/0192603 A1* | | 7/2009 | Ryan ..................... A61F 2/2496 623/2.11 |
| 2010/0160832 A1* | | 6/2010 | Braido ............... A61B 5/02007 600/587 |
| 2010/0249661 A1* | | 9/2010 | Righini .................. A61B 5/103 600/587 |

OTHER PUBLICATIONS

International Bureau, International Search Report for International Application No. PCT/US10/028830, Jun. 9, 2010, pp. 1-2, Geneva, Switzerland.

International Bureau, Written Opinion of the International Search Authority for International Application No. PCT/US10/028830, Jun. 9, 2010, pp. 1-7, Geneva, Switzerland.

International Bureau, International Preliminary Report for Patentability Chapter I for International Application No. PCT/US10/028830, Jun. 9, 2010, pp. 1-9, Geneva, Switzerland.

* cited by examiner

US 9,763,602 B2

INTRA-OPERATIVE HEART SIZE MEASURING TOOL

CROSS-REFERENCE TO RELATED APPLICATIONS

This application is a continuation of U.S. patent application Ser. No. 14/698,689 filed Apr. 28, 2015, which is a continuation of U.S. application Ser. No. 13/261,173, filed on Jun. 29, 2012 (now U.S. Pat. No. 9,044,169 Issued Jun. 2, 2015), which is a United States national stage entry of International Application no. PCT/US2010/028830 filed Mar. 26, 2010 and entitled "Intra-Operative Heart Sizing Tool," which claims priority to U.S. provisional patent application No. 61/164,183 filed Mar. 27, 2009. The contents of these prior applications are incorporated herein by reference in their entirety as if set forth verbatim.

FIELD OF THE INVENTION

The invention is a tool for measuring the size of a heart in situ.

BACKGROUND OF THE INVENTION

Cardiac support devices (CSDs) used to treat heart disease are generally known and disclosed, for example, in International Publication No. WO 2008/003034 which is incorporated herein by reference in its entirety. CSDs and tools and methods for surgically delivering or implanting the devices are also generally known and disclosed, for example, in International Publication No. WO 2008/011411 which is incorporated herein by reference in its entirety.

Sizes of diseased hearts can vary. Accordingly, CSDs come in a range of sizes. Prior to the delivery procedure, a surgeon will typically measure the size of the patient's heart, and select an appropriately sized CSD. One known approach for measuring the patient's heart size is through CT imaging under fluoroscopy. Heart size measuring tools are also disclosed in the Vanden Hoek et al. U.S. Pat. No. 6,575,921 and the Krueger U.S. Pat. No. 6,179,791.

There is, however, a continuing need for improved measuring tools and associated methods. In particular, there is a need for heart size measuring tools and methods that are accurate and efficient to perform.

SUMMARY OF THE INVENTION

The invention is an improved intra-operative heart size measuring tool. The tool can be efficiently used to provide accurate measurements of a heart size. One embodiment of the tool includes a tubular body, a flexible measuring cord having length indicia, a measuring cord support mechanism and an actuating mechanism. The actuating mechanism moves the measuring cord support mechanism between retracted and extended states with respect to the body to drive the measuring cord between a collapsed position and a measuring position. When the measuring cord is in the measuring position the measuring cord extends around a portion of the heart to be measured. Another embodiment of the invention includes a scale that can be used in connection with the indicia on the measuring cord to provide a reading of the heart size.

DETAILED DESCRIPTION

Figure 1:
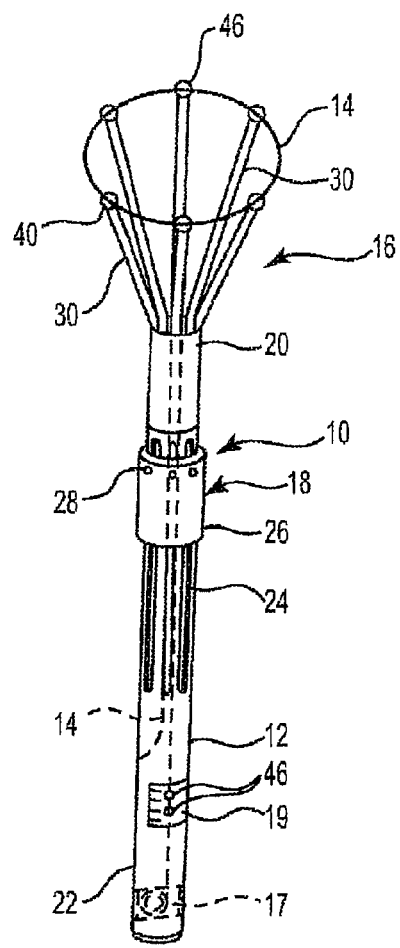
FIG. 1 is an isometric illustration of a heart size measuring tool in accordance with one embodiment of the invention, with the measuring cord support mechanism shown in the extended position.
Figure 2:
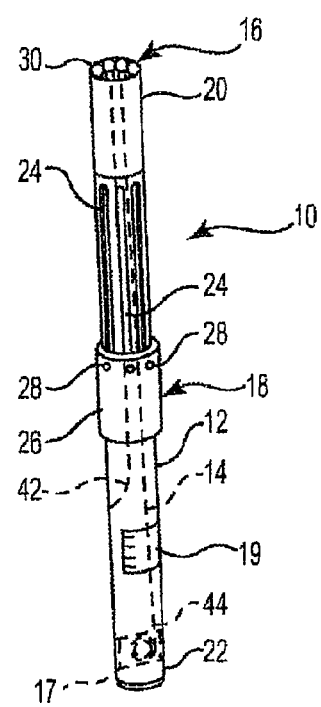
FIG. 2 is an isometric illustration of the heart size measuring tool shown in FIG. 1, with the measuring cord support mechanism shown in the retracted position.
Figure 3:
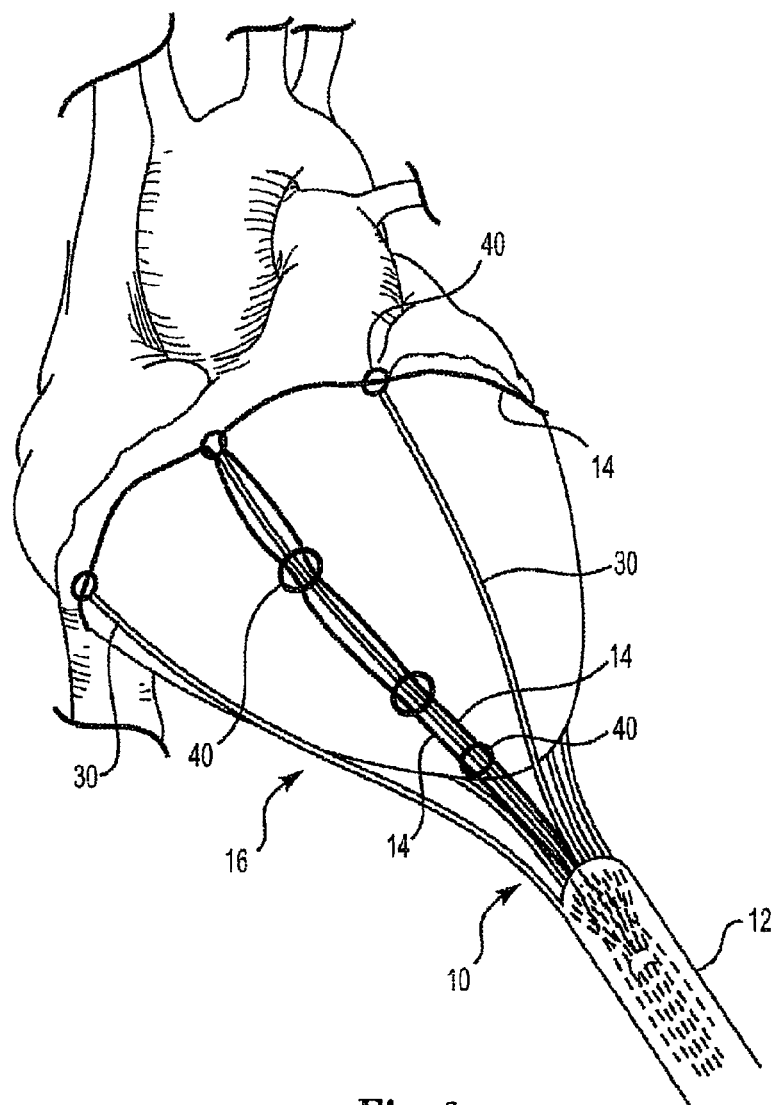
FIG. 3 is an isometric illustration of the distal end of the measuring tool shown in FIG. 1, with the measuring cord support mechanism in the extended state and the measuring cord in a measuring position around the atrioventricular groove of a heart.

One embodiment of an intra-operative heart size measuring tool 10 in accordance with the present invention is shown in FIGS. 1-3. Measuring tool 10 includes body 12, measuring cord 14, measuring cord support mechanism 16, actuating mechanism 18, measuring cord retraction mechanism 17 and scale 19. Body 12 is a generally tubular member having a distal end 20, proximal end 22 and a plurality of elongated slots 24 (six are shown in the illustrated embodiment) extending through the body at a location adjacent to the actuating mechanism 18. Actuating mechanism 18 includes a handle 26 that is slidably mounted to the body 12. Engagement structures such as pins 28 on the handle 26 extend into the slots 24. Measuring cord support mechanism 16 includes a plurality (six are shown) of support members 30 within the body 12. Proximal ends (not visible) of each of the support members 30 are connected to the pins 28 within the body 12. Other embodiments (not shown) include other structures operatively coupling the handle 26 to the support members 30.

Support members 30 are elongated and resilient members. Each of the support members 30 includes one or more guides 40, shown as loops in the illustrated embodiment, for supporting the measuring cord 14. In the illustrated embodiment, each of the support members 30 has a guide 40 located near the distal end of the support member. One of the support members 30 also has a number of guides 40 at spaced locations along its length. As perhaps best shown in FIG. 3, measuring cord 14 extends through the guides 40 at the ends of the support members 30, and into the body 12 through the guides 40 along the length of the one support member. One end 42 of the measuring cord 14 is fixedly mounted to the body 12. The other end 44 of the measuring cord 14 is mounted to the retraction mechanism 17. Cord retraction mechanism 17 can be a spring-loaded spool that is biased to wind up slack portions of the measuring cord 14. Measuring cord 14 has indicia such as graduated length markings 46 in the embodiment shown in FIG. 1.

Handle 26 is actuated to drive the measuring cord support mechanism 16 between a first or retracted state shown in FIG. 2 and a second or extended state shown in FIGS. 1 and 3. In the retracted state shown in FIG. 2, the support members 30 are in a reduced-diameter configuration. In the illustrated embodiment this configuration is achieved by the actuating mechanism 18 withdrawing the support members 30 completely into the distal end 20 of the body 12. In other embodiments (not shown) the support members 30 extend partially out of the body 12 when the support mechanism 16 is in its retracted state. When the measuring cord support mechanism 16 is in the retracted state the support members 30 pull the measuring cord 14 into a collapsed position. Retraction mechanism 17 can retract and retain portions of the measuring cord when the support mechanism 16 is in the retracted state. When the measuring cord support mechanism 16 is in the extended state shown in FIGS. 1 and 3, the support members 30 extend from the distal end 20 of the body 12. The measuring cord 14 is thereby forced out of the body 12, with portions of the measuring cord being withdrawn from retraction mechanism 17 and sliding through the guides 40.

Tool 10 is used to measure the size of a patient's heart. In one embodiment the measurements taken by the tool 10 can be used to select the size of a cardiac support device (CSD) being applied to the patient's heart. Use of the tool 10 will typically begin with the measuring cord support mechanism 16 in the retracted state. The distal end 20 of the tool 10 can then be inserted through an opening in the patient's chest and pericardium (not shown) and positioned at a measurement position at the apex of the patient's heart. For example, the tool 10 can be inserted through a minimal access site such as a thoracotomy. Fluoroscopic guidance can be used to position the tool 10. The tool 10 can be sized or otherwise configured so that the handle 26 and scale 19 are located outside of the patient's body when the distal end 20 of the tool is located at the measurement position. The handle 26 is then actuated to drive the measuring cord support mechanism 16 to the extended state with the support members 30 extending around the heart and positioning the measurement cord 14 in the measurement position around the heart at the target location to be measured. In this and other embodiments the support members 30 can be telescoping. When measuring the heart for CSD sizing, for example, the circumference of the heart at the atrioventricular (A-V) groove will typically be measured. However, the circumference of the heart at locations in addition or as an alternative to the A-V groove can be measured. Once the measuring cord 14 is positioned in this manner, the circumference of the heart can be read from scale 19 based on the indicia 46 on the measuring cord. For example, the indicia 46 can be calibrated in such a manner that the indicia closest to a marker on scale 19 represents the circumference of the heart at the target location. After the measurement is taken, the handle 26 can be actuated to return the measuring cord support mechanism 16 to the retracted state, and the tool 10 withdrawn from the patient.

The tool 10 is described above as a dedicated measurement instrument. In other embodiments (not shown), the measuring cord can be incorporated onto other tools such as the CSD delivery tools described in the international applications referred to above in the background section. For example, the measuring cord can be incorporated onto the retractable/extendable CSD deployment mechanism shown in the international applications (i.e., the deployment mechanism would serve a dual function), or a separate measuring cord support mechanism in addition to the CSD deployment mechanism can be used.

The measuring cord 14 can be radiopaque to enhance its visibility under fluoroscopic or other imaging modalities during the use of tool 10 (e.g., as an aide to positioning the measuring cord). In other embodiments (not shown), the measuring cord 14 can have radiopaque or other markers at predetermined locations. These markers can be viewed under an imaging modality (e.g., during an echocardiogram (ECHO) or transesophageal echo (TEE)) to determine the size of the heart. The markers can be made distinguishable from one another to enhance the accuracy of the measurement reading. In still other embodiments (not shown) the measuring cord can be color coded to facilitate measurement readings. Yet other embodiments of the invention make use of other structures or approaches for determining the size of the heart based on the length of the cord extended during the deployment of the measuring tool and for providing a visual display representative of the measured heart size. For example, an instrument operatively coupled to the retraction mechanism can measure and provide a visual indication of heart size based on the length of the measuring cord withdrawn from the retraction mechanism. Windows with indicia or other features enabling measurement readings can also be located on the support members 30.

Figures 4, 5:
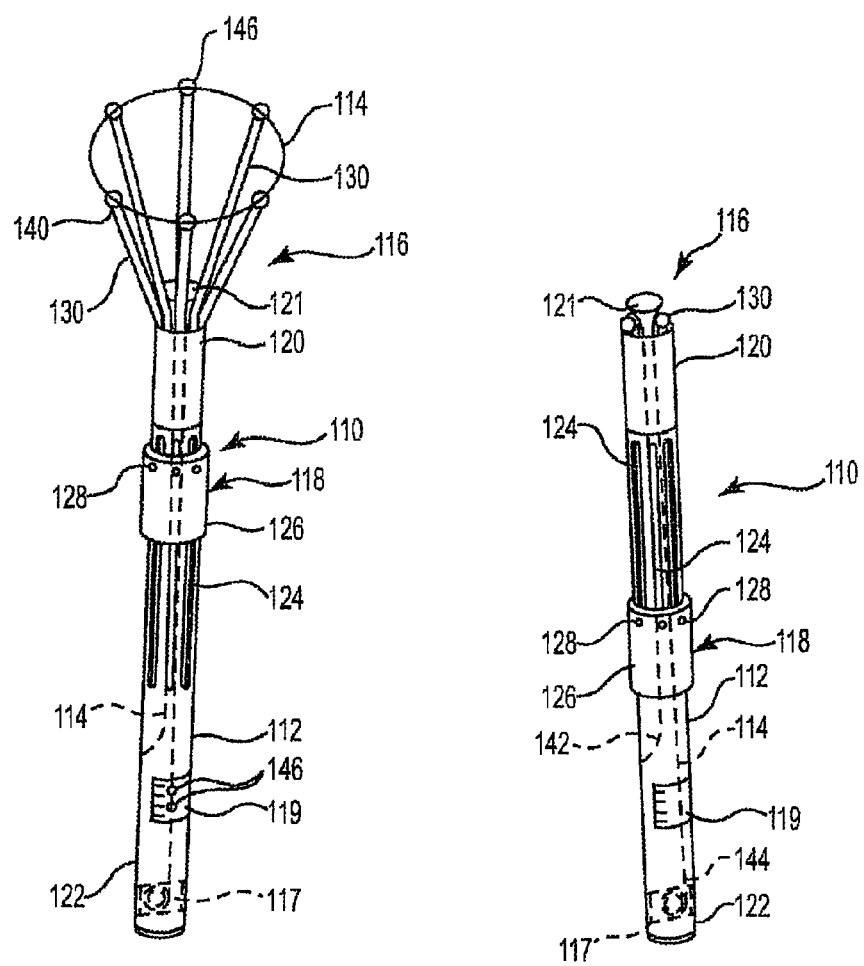
FIG. 4 is an isometric illustration of a heart size measuring tool in accordance with another embodiment of the invention, having a suction cup and shown with the measuring cord support mechanism in the extended position.
FIG. 5 is an isometric illustration of the heart size measuring tool shown in FIG. 4, with the measuring cord support mechanism shown in the retracted position.

FIGS. 4 and 5 illustrate a measuring tool 110 in accordance with another embodiment of the invention. As shown, a suction cup 121 is located on the distal end 120 of measuring tool 110. The suction cup 121 is connected to a vacuum source through a tube (not shown) that extends through all or a portion of body 112. A valve (not shown) on body 112 or elsewhere can be used to control the application of the vacuum to the suction cup 121. The suction cup 121 functions as a releasable suction device to hold the measuring tool 110 on the patient's heart and to stabilize the heart during the measurement procedure (including during the deployment and withdrawal of the measuring cord support mechanism 116). For example, when the measuring cord support mechanism 116 is in the retracted state shown in FIG. 5, the suction cup 121 can be positioned adjacent to the apex of the patient's heart and connected to the vacuum source to secure the body 112 to the heart. Support mechanism 116 can then be deployed to the extended state while the suction cup 121 provides traction holding the body 120 to the heart. The vacuum source can be disconnected from the suction cup 121 when the traction provided by the cup is no longer needed (e.g., after the support mechanism 116 is returned to its retracted state). Other than the inclusion of the suction cup 121 and any associated structures such as the vacuum tube and valve, tool 110 can be substantially the same as or similar to tool 10 described above, and similar features are identified by similar reference numbers.

Figure 6:
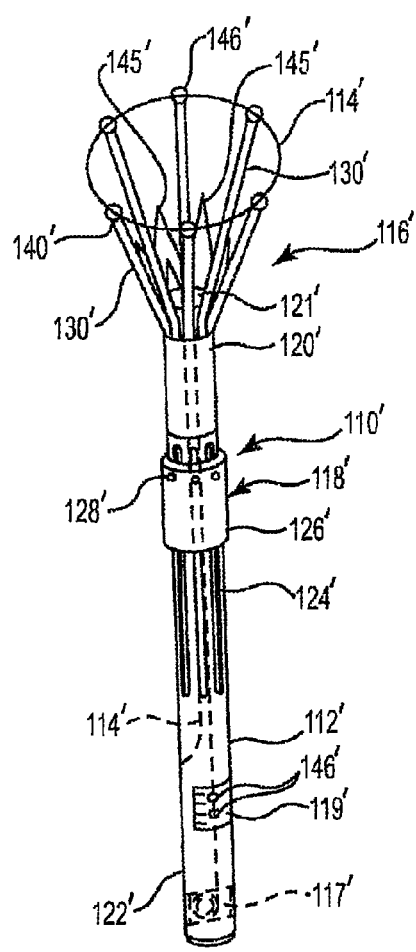
FIG. 6 is an isometric illustration of a heart size measuring tool in accordance with another embodiment of the invention, having ties between the support members of the measuring cord support mechanism and shown with the support mechanism in the extended position.
Figure 7:
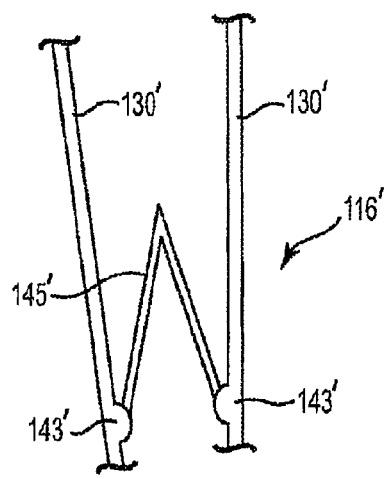
FIG. 7 is a detailed illustration of a pair of support members and a tie of the measuring tool shown in FIG. 6.

FIG. 6 is an illustration of a heart size measuring tool 110' in accordance with another embodiment of the invention having ties 145' connecting adjacent support members 130'. FIG. 7 is a detailed illustration of one of the ties 145'. The ties 145' open and collapse with the support members 130' when the support mechanism 116' is moved between the extended and retracted states, and help keep the adjacent support members properly spaced (e.g., generally equidistant) from one another. The ties 145' provide this function by providing resistance to any forces that might tend to cause the support members 130' to collapse toward one another. In the illustrated embodiment the ties 145' are folded elongated members such as malleable metal strips having their opposite ends attached to the support members 130' (e.g., by welds or adhesive 143'). Other structures for maintaining the spacing between the support members 130' can be used in other embodiments (not shown). For example, physical stops on the measurement cord that engage the guides on the support members can be located at predetermined spaced-apart locations on the measurement cord to provide or limit the maximum distance between the support members. Other than the inclusion of the ties 145', tool 110' can be substantially the same as or similar to tool 110 described above, and similar features are identified by similar reference numbers.

In this and other embodiments, the support members can have stiffnesses that vary along the length of the members. Alternatively or in addition, the stiffness of the support members can be different in different directions. For example, variable thickness can be provided by internal movable stylets, inflation, changing thicknesses and changing cross-sectional shapes along the length of the members. By way of example, the dimension of the members in a radial direction with respect to a longitudinal axis through the tool 10 can be smaller than the dimension in the circumferential direction, enabling the support members to be relatively rigid in connection with movement around the heart, yet relatively flexible when moved toward or away from the heart. The support members can also be malleable (e.g., metal or metal reinforced polymer) so they can be shaped by the physician or other person operating the tool.

Figure 8:
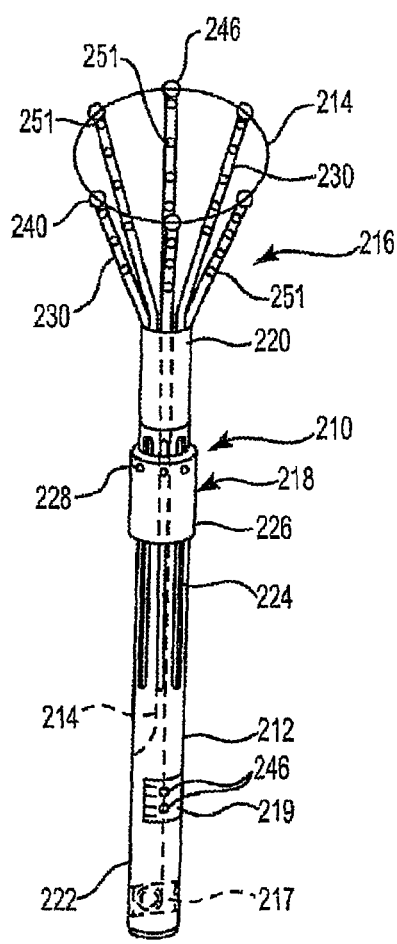
FIG. 8 is an isometric illustration of a heart size measuring tool in accordance with another embodiment of the invention, having radiopaque markers on the support members of the measuring cord support mechanism and shown with the support mechanism in the extended position.

FIG. 8 is an illustration of heart size measuring tool 210 in accordance with another embodiment of the invention. One or more radiopaque or other markers 251 (e.g., piezoelectric crystals) are located at spaced apart locations along the length of the support members 230. A plurality of markers 251 are shown in each support member 230 in the illustrated embodiment, including a marker on the distal end of the support members. The markers 251 can be coded or otherwise made uniquely identifiable or distinguishable from one another. Fluoroscopic, ECHO, TEE or other appropriate imaging modalities can be used to image the measuring tool 210 when the support members 230 are positioned on the patient's heart, and the locations and spacing of the markers 251 can be used to determine the size of the heart. For example, a fluoroscopic image taken generally parallel to the longitudinal axis of the tool 210 will show the markers 251 in a generally circular pattern. The external diameter of the hemi can be interpolated and estimated from this image. Other than the inclusion of the markers 251, tool 210 can be substantially the same as or similar to tool 10 described above, and similar features are identified by similar reference numbers. Still other embodiments of the invention (not shown) have a support mechanism with markers such as those of the embodiment shown in FIG. 8, but do not include the measuring cord and associated components such as the retraction mechanism and scale.

Markers 251 can then enable fluoroscopic or other imaging-based estimates of the longitudinal length of the heart and/or CSD. Dimension information for both length and circumference are available, facilitating the selection of the most appropriately-sized CSD for implantation. Similarly, this feature will enable "mapping" of the heart. The circumference of the heart at planes parallel to the base at locations between the base and apex of the heart can be measured. This information can be used to estimate the surface area/shape of the heart. This additional information can further enhance correct CSD size selection.

Figure 9:
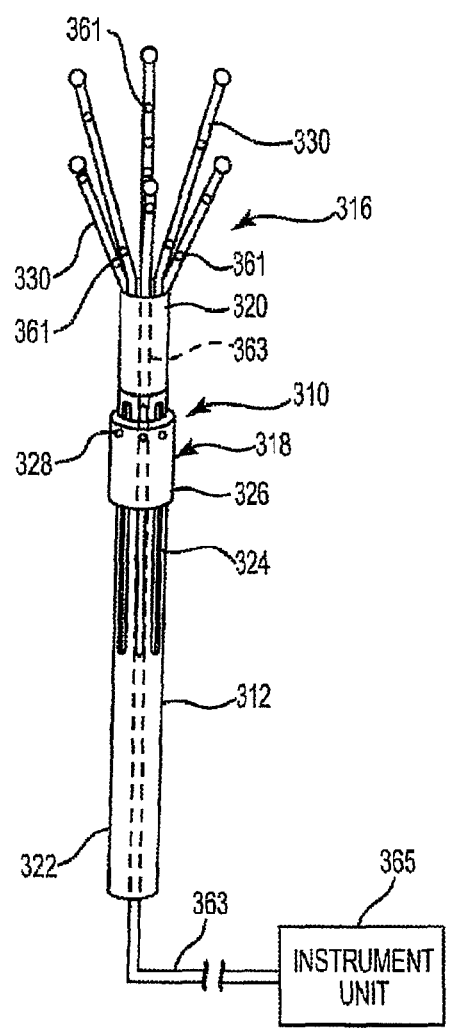
FIG. 9 is an isometric illustration of a heart size measuring tool in accordance with another embodiment of the invention, having deflection sensors on the support members and shown with the support mechanism in the extended position.

FIG. 9 is an illustration of a heart size measuring tool 310 in accordance with another embodiment of the invention. As shown, the tool 310 includes one or more deflection sensors 361 located on each support member 330 (a plurality of sensors 361 are shown on each support member in the illustrated embodiment). Sensors 361, which can for example be strain gauge sensors, are operatively connected to an instrument unit 365 (e.g., by wires, not shown, through cable 363). The instrument unit 365 provides any drive power or signals needed for operation of the sensors 361. When the support mechanism 316 is positioned around the patient's heart, the support members 330 will be deflected by amounts representative of the size of the heart. Deflection signals representative of the deflection of the support members are received and processed by the instrument unit 365 to provide information (e.g., a display) representative of the heart size. Other than the inclusion of sensors 361 and instrument unit 365, and the lack of a measuring cord and associated components such as the retraction mechanism and scale, measuring tool 310 can be substantially the same as or similar to tool 110 described above, and similar features are identified by similar reference numbers. In still other embodiments (not shown) the sensors on the support members include transmitting and receiving devices coupled to an instrument unit. In these embodiments the instrument unit can use Doppler or other methodologies to detect the relative positioning of the sensors and produce a heart size measurement.

Figure 10:
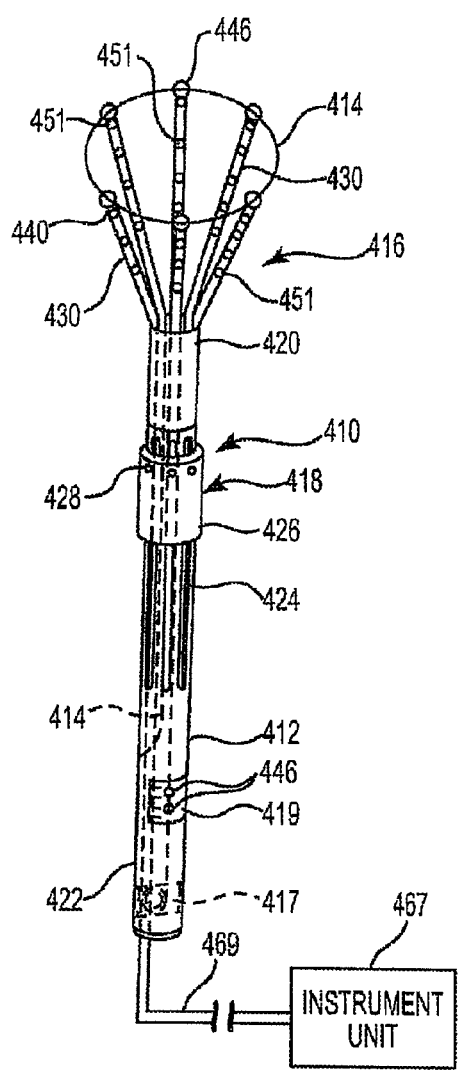
FIG. 10 is an isometric illustration of a heart size measuring tool in accordance with another embodiment of the invention, having EEG or other sensor electrodes on the support members and shown with the support mechanism in the extended position.

FIG. 10 is an illustration of a heart size measuring tool 410 in accordance with another embodiment of the invention. As shown, the tool 410 includes a plurality of sensor electrodes 451 located on each support member 430. Sensor electrodes 451 are connected to an instrument unit 467 by wires (not shown) through cable 469. Sensor electrodes 451 and instrument unit 467, which can, for example, be electrocardiogram (ECG) electrodes and instrumentation, are used to map the electrical potentials across the surface of the heart while the tool 410 is also used to measure the heart size. The measuring tool 410 can be moved (e.g., rotated) to place the sensor electrodes 451 at different locations on the heart to enable electrical potential measurements across the surface of the heart. Other than the inclusion of sensor electrodes 451 and instrument unit 467, tool 410 can be substantially the same as or similar to tool 10 described above, and similar features are identified by similar reference numbers. The sensor electrodes 451 can also be used to locate the measuring tool 410. The electrocardiogram signal produced by the heart has different characteristics above and below the A-V groove. By monitoring these signals using the sensor electrodes 451, and in particular using the signals from electrodes near the ends of the support members 430, the location of the A-V groove can be identified.

Figure 11:
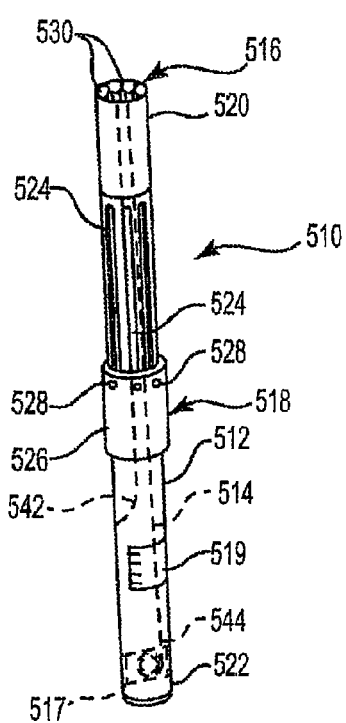
FIG. 11 is an is isometric illustration of a heart size measuring tool in accordance with another embodiment of the invention, shown with the support mechanism in the retracted position.
Figure 12:
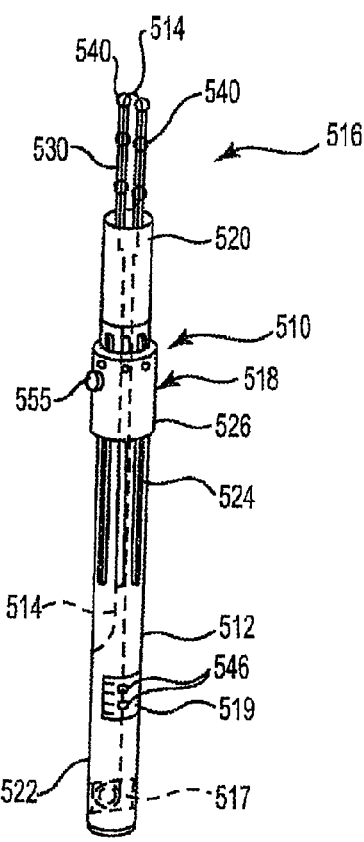
FIG. 12 is an isometric illustration of the heart size measurement tool shown in FIG. 11, with the support mechanism in the extended and unactuated position.
Figure 13:
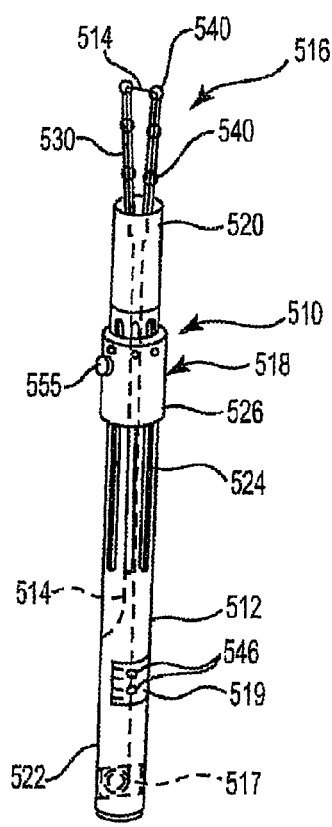
FIG. 13 is an isometric illustration of the heart size measurement tool shown in FIG. 11, with the support mechanism in the extended and partially actuated position.

FIGS. 11-13 are illustrations of a heart size measuring tool 510 in accordance with another embodiment of the invention. As shown, the tool 510 includes a support mechanism 516 having two support members 530. The measuring cord 514 extends from the body 512 along each support member 530 through guides 540, and between the guides 540 at the ends of the support members. Support members 530 are connected to actuating mechanism 518. Actuating mechanism 518 can be actuated to move the support members 530 between a retracted position shown in FIG. 11 and an extended position shown in FIGS. 12 and 13.

Measuring tool 510 also includes a measurement actuator 555 coupled to one or both of the support members 530. The measurement actuator 555 is operated to drive the support members 530 between the unactuated measurement position shown in FIG. 12 to an actuated measurement position. As shown in FIG. 12, the support members 530 can be positioned adjacent to one another in the unactuated measurement position. The support members 530 are shown in a partially actuated position in FIG. 13, with the support members spaced from one another to extend the measuring cord 514. The support members 530 can have features of any of the embodiments described above.

Figure 14:
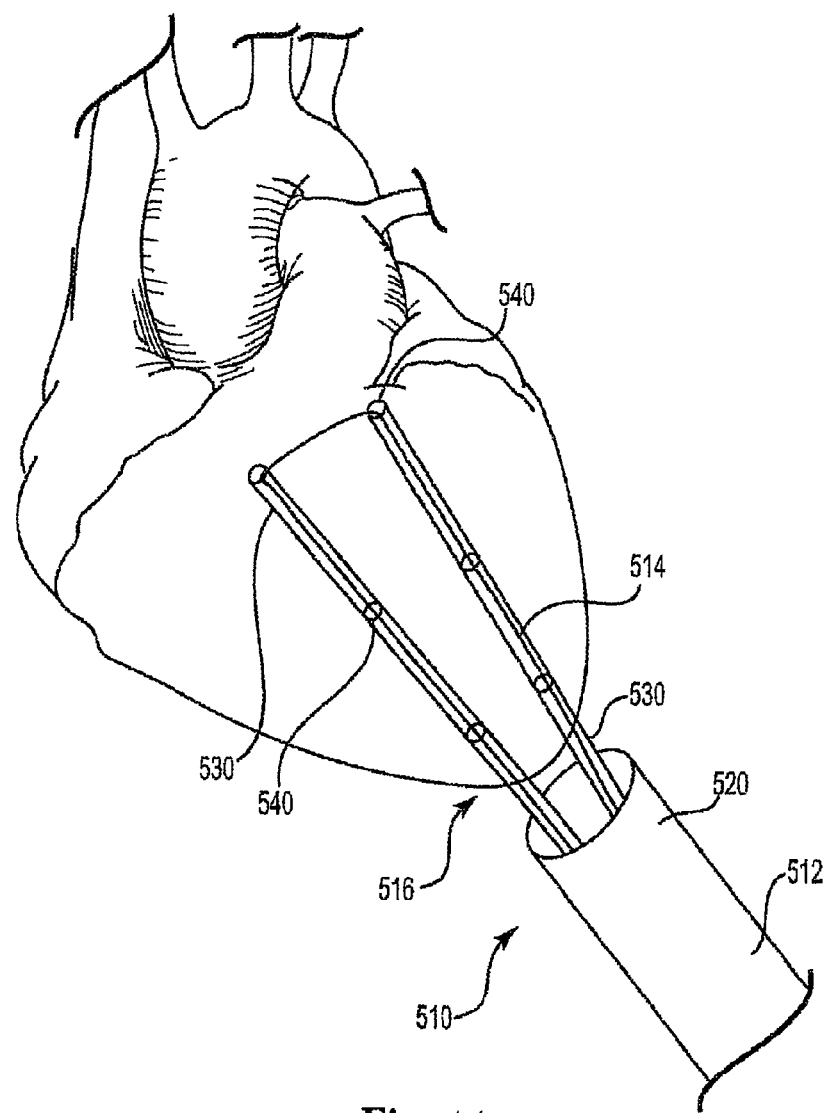
FIG. 14 is an isometric illustration of the distal end of the measuring tool shown in FIGS. 11-13, with the measuring cord support mechanism in the extended state and partially actuated to extend the measuring cord around a portion of the atrioventricular groove of a heart.
Figure 15:
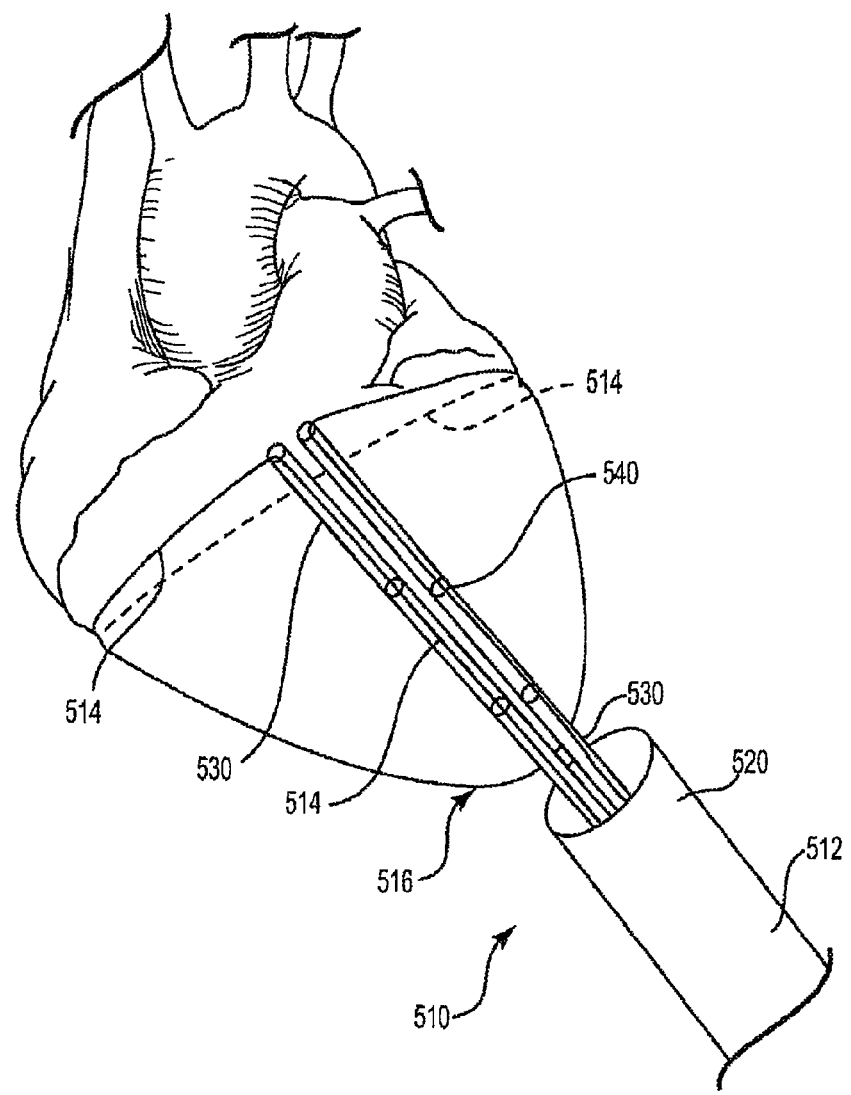
FIG. 15 is an isometric illustration of the distal end of the measuring tool shown in FIGS. 11-13, with the measuring cord support mechanism in the extended state and fully actuated to extend the measuring cord around the atrioventricular groove of a heart.

The operation of measuring tool 510 can be described with reference to FIGS. 11-15. After the distal end 520 of the body 512 is positioned adjacent to the heart, the actuating mechanism 518 is operated to move the support mechanism 516 from the retracted position shown in FIG. 11 to the extended position shown in FIG. 12. The tool 510 is then manipulated to position the distal ends of the support members 530 at the target measurement location on the heart. When the support mechanism 516 is initially moved to the extended position the support members 530 can be in an unactuated position with respect to one another. The measurement actuator 555 is then operated to move the support members 530 with respect to one another to extend the measuring cord 514 along the measurement target on the heart. In one embodiment of the invention, one of the support members 530 remains stationary, and the other support member is revolved around the heart. FIG. 14 shows the support members 530 in a partially actuated position with the measuring cord 514 extended along a portion of the heart near the A-V groove. FIG. 15 shows the support members 530 fully actuated, with the measuring cord 514 in the measurement position extended around the heart at the A-V groove. The measured dimension of the heart can be read from scale 519 when the measuring cord 514 is in the measurement position. Magnets or other structures on the support members 530 can releasably lock the support members together after one of the support members has fully moved around the heart with respect to the other support member and contacts the other support member, thereby aiding the measurement. After the measurement is completed, the measurement actuator 555 can be operated to return the support members 530 to the unactuated position. The actuating mechanism 518 can then be operated to retract the support mechanism before removing the tool from the patient. Other than the support mechanism 516 and measurement actuator 555, tool 510 can be substantially the same as or similar to tool 10 described above, and similar features are identified by similar reference numbers.

Measuring tools in accordance with the invention offer a number of important advantages. They are relatively efficient to operate and make use of surgical access incisions that will be used for the delivery of the CSD. The tools are capable of providing accurate measurements at any desired location on the heart. Enhanced CSD sizing is enabled since measurements of the heart size can be made relatively close in time to the delivery of the CSD. The need for other imaging modalities used for heart size measurement can be eliminated. Other functionality such as electrical mapping can be provided concurrently.

Although the present invention has been described with reference to preferred embodiments, those skilled in the art will recognize that changes can be made in form and detail without departing from the spirit and scope of the invention. For example, more than one measurement cord can be used. Other approaches for mounting the measuring cord to the body, and for reading the measurements from the cord, can also be used. Features of the different embodiments of the invention described above can also be combined in different combinations. For example, the ties of the embodiment shown in FIG. 6 can be incorporated into other embodiments of the invention.

The invention claimed is:

1. A heart measurement tool comprising:
a tubular body;
a suction cup disposed at a distal end of the tubular body;
a plurality a elongate support members having respective distal end portions;
a flexible measuring cord supported by a distal end portion of at least one of the elongate support members;
an actuating mechanism slidably positionable to move the distal end portions of the plurality of elongate support members proximally and distally of the suction cup;
a scale disposed on a proximal portion of the heart measurement tool; and
a cord tension control mechanism that establishes a maximum tension of the flexible measuring cord.

2. The heart measurement tool of claim 1, wherein the cord tension control mechanism comprises a spring.

3. The heart measurement tool of claim 1, wherein the cord tension control mechanism comprises a spring-loaded spool that is biased to wind up slack portions of the flexible measuring cord.

4. The heart measurement tool of claim 1, wherein the scale is located on a portion of the tubular body outside of the patient when the flexible measuring cord is in the measuring position.

5. The heart measurement tool of claim 1, wherein the plurality of elongate support members comprises at least three elongate support members.

6. The heart measurement tool of claim 1, wherein the actuating mechanism is attached to the proximal ends of each of the elongate support members.

7. The heart measurement tool of claim 1, wherein the tubular body defines a lumen that extends from the suction cup through all of the tubular body.

8. The heart measurement tool of claim 1, wherein the plurality of elongate support members comprises at least three elongate support members, and wherein the flexible measuring cord is supported by the distal end portion of each of the at least three elongate support members.

9. The heart measurement tool of claim 1, wherein the distal end portion of each of the elongate support members includes a guide through which the flexible measuring cord extends.

10. The heart measurement tool of claim 1, wherein the heart measurement tool is reconfigurable between a first configuration in which the plurality of elongate support members extend distally beyond the suction cup and a second configuration in which the plurality of elongate support members are retracted proximally of the suction cup.

11. The heart measurement tool of claim 10, wherein the while the heart measurement tool is configured in the first configuration, the plurality of elongate support members extend radially outward from the tubular body.

12. The heart measurement tool of claim 10, wherein the while the heart measurement tool is configured in the first configuration, the actuating mechanism is closer to the suction cup than while the heart measurement, tool is configured in the second configuration.

\* \* \* \* \*

UNITED STATES PATENT AND TRADEMARK OFFICE
CERTIFICATE OF CORRECTION

PATENT NO. : 9,763,602 B2  
APPLICATION NO. : 15/223973  
DATED : September 19, 2017  
INVENTOR(S) : Aaron J. Hjelle et al.

Page 1 of 1

It is certified that error appears in the above-identified patent and that said Letters Patent is hereby corrected as shown below:

In the Claims

Column 8, Line 33, Claim 1, delete "a elongate" and insert -- of elongate --;

Column 9, Line 5, Claim 10, after wherein delete "the";

Column 9, Line 12, Claim 11, after wherein delete "the";

Column 9, Line 16, Claim 12, after wherein delete "the";

Column 9, Line 19, Claim 12, after measurement, delete ",";

Signed and Sealed this
Ninth Day of July, 2019

Andrei Iancu
*Director of the United States Patent and Trademark Office*